United States Patent
Kuchikata et al.

(12)
(10) Patent No.: US 6,228,807 B1
(45) Date of Patent: May 8, 2001

(54) GLYPHOSATE FORMULATIONS

(75) Inventors: Masuo Kuchikata, Ibaraki (JP); Erhard J. Prill, Kirkwood; Ronald O. Richardson, Ellisville, both of MO (US); Tatsuo Sato, Tokyo (JP); John M. Surgant, Clayton; Daniel R. Wright, St. Louis, both of MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 08/899,297

(22) Filed: Jul. 23, 1997

Related U.S. Application Data

(63) Continuation of application No. 08/726,538, filed on Oct. 7, 1996, now abandoned, which is a continuation of application No. 08/557,371, filed on Nov. 13, 1995, now abandoned, which is a continuation of application No. 07/625,516, filed on Dec. 11, 1990, now abandoned, which is a continuation of application No. 07/292,499, filed on Dec. 30, 1988, now abandoned.

(51) Int. Cl.[7] ................................................. A01N 33/04
(52) U.S. Cl. ........................................ 504/206; 71/DIG. 1
(58) Field of Search .......................... 504/206; 71/DIG. 1

(56) References Cited

U.S. PATENT DOCUMENTS

| | | | |
|---|---|---|---|
| 3,224,865 | 12/1965 | Carlson | 71/2.6 |
| 3,245,775 | 4/1966 | Pfeiffer | 71/2.6 |
| 3,737,551 | * 6/1973 | Karsten et al. | 71/DIG. 1 |
| 3,799,758 | 3/1974 | Franz | 71/86 |
| 3,920,442 | * 11/1975 | Albert et al. | 71/92 |
| 3,954,439 | * 5/1976 | Papamichael et al. | 71/DIG. 1 |
| 3,977,860 | 8/1976 | Franz | 71/86 |
| 4,025,332 | 5/1977 | Franz | 71/86 |
| 4,140,513 | 2/1979 | Prill | 504/206 |
| 4,315,765 | 2/1982 | Large | 504/206 |
| 4,397,676 | 8/1983 | Bakel | 504/206 |
| 4,405,531 | 9/1983 | Franz | 260/501 |
| 4,481,026 | 11/1984 | Prisbylla | 504/190 |
| 4,486,358 | 12/1984 | Moser | 260/502.5 F |
| 4,507,250 | 3/1985 | Bakel | 562/17 |
| 4,840,659 | * 6/1989 | Franz | 71/86 |

FOREIGN PATENT DOCUMENTS

| | | | |
|---|---|---|---|
| 0143547 | * 6/1985 | (EP) | 71/86 |
| 0 206 537 | 12/1986 | (EP) | A01N/57/20 |
| 8704595 | * 8/1987 | (EP) | . |
| 0 256 608 | 2/1988 | (EP) | A01N/25/14 |
| 255760 | 2/1988 | (EP) | B01J/13/02 |
| 0 290 416 | 11/1988 | (EP) | A01N/25/30 |
| 204146 | 11/1988 | (EP) | . |
| 62-175407 | 8/1987 | (JP) | A01N/57/20 |
| 62-175408 | 8/1987 | (JP) | A01N/57/20 |
| 0145205 | * 6/1988 | (JP) | . |
| 63-145205 | 6/1988 | (JP) | A01N/57/20 |
| 87/04595 | 8/1987 | (WO) | A01N/57/20 |
| WO 87/04712 | 8/1987 | (WO) | C07F/9/38 |

OTHER PUBLICATIONS

Chemical Patents Index Abstract 87–253854/36 (1987).
Derwent Abstract 85–136411/23 (1985).
Research Disclosure Publication 27161, "Novel Glyphosate acid wettable powder formulation effective in control of weeds," Nov. 1996.
Chemical Abstracts 103: 191395K (1985) Davydov, A.M.; Vechtomova, Y.N.; Banzunova, G.F. (USSR). Sachch. Rast. (Moscow) 1985, (9), 40–1 (Russ).
McCutcheon's Detergents & Emulsifiers 1971 Annual, Allured Publishing Corporation, 1971. p. 42.*

* cited by examiner

*Primary Examiner*—Samuel Barts
(74) *Attorney, Agent, or Firm*—Arnold White & Durkee; James C. Forbes

(57) ABSTRACT

This invention relates to dry, water soluble, agriculturally acceptable herbicidal compositions, to a herbicidal method of use thereof and and to a process for preparing such compositions. This invention also relates to dry, water soluble and/or water dispersible, agriculturally acceptable herbicidal compositions containing two or more herbicides, a herbicidal method of use thereof and to a process for preparing such compositions.

9 Claims, No Drawings

GLYPHOSATE FORMULATIONS

This application is a continuation of application Ser. No. 08/726,538, filed Oct. 7, 1996, now abandoned, which is a continuation of application Ser. No. 08/557,371, filed Nov. 13, 1995, now abandoned, which is a continuation of application Ser. No. 07/625,516, filed Dec. 11, 1990, now abandoned, which is a continuation of application Ser. No. 07/292,499, filed Dec. 30, 1988, now abandoned.

FIELD OF THE INVENTION

This invention relates to dry, water soluble, agriculturally acceptable herbicidal compositions useful for killing and/or controlling weeds and to a process for preparing such compositions. This invention also relates to dry, water soluble or water dispersible, granular, agriculturally acceptable herbicidal compositions containing two or more herbicides, herbicidal methods of use thereof and to a process for preparing such compositions.

DESCRIPTION OF THE PRIOR ART

Glyphosate (N-phosphonomethylglycine) is well known in the art as an effective herbicide. It is also known that glyphosate, an organic acid, is relatively insoluble in water. Glyphosate is typically formulated as a water-soluble salt, especially as the isopropylamine salt (IPA salt) to kill or control weeds or plants. Glyphosate is typically sold commercially as an aqueous concentrate.

Various salts of glyphosate, methods for preparing salts of glyphosate, formulations of glyphosate and methods of use for killing and controlling weeds and plants are disclosed in U.S. Pat. Nos. 3,799,758 and 4,405, 531 issued to John E. Franz on Mar. 26, 1974 and Sep. 20,1983 respectively. Other US patents which disclose salts of glyphosate include U.S. Pat. No. 4, 315,765 issued to George B. Large on Feb. 16, 1982, U.S. Pat. No. 4,507,250 issued to Izak Bakel on Mar. 26, 1985, U.S. Pat. No. 4,397,676 issued to Izhak Bakel on Aug. 9, 1983, U.S. Pat. No. 4, 481, 026 issued to Michael P. Prisbylla on Nov. 6, 1984 and, U.S. Pat. No. 4, 140,513 issued to Erhard J. Prill on Feb. 20, 1979. The aforementioned patents are incorporated herein in their entirety by reference.

EPO published patent application 204146 discloses a herbicidal composition comprising (a) 2-(4-chloror-2-fluror 5-propargyloxyphe-nyl)-5,6,7, 8-tetrahydro-1H-1,2,4-triazolo (1,2-s)phridazine -1,3,-2H-dione (I), with (b) glyphosate (i) glufosinate (ii) bialaphos (iii) and/or paraquat (iv) or their salts and an inert carrier or diluent.

EPO published patent application 255760 discloses a granule shaped agricultural composition prepared by introducing to the top of a drying tower, a mixture of the agricultural chemical, an anionic surfactant and optionally one or more additives in the form of a concentrated solution or an aqueous slurry.

Published Japanese patent applications J62175407 and J62175408 disclose a herbicide containing solid carrier, additives and herbicidal component and has a particle size of 48-150 mesh. Disclosed herbicidal components are ((3-amino-3-carboxy)propyl-1)methylphosphonic acid, N-(phosphonomethyl)glycine, (2-amino-4-methylphosphino-butyral) alanylalanine and their salts.

Published European Patent Application 0 206 537 discloses a solid, substantially non-hygroscopic, phytoactive composition comprising an intimate mixture of a phytoactive N-phosphonomethyl-N-carboxymethyl compound and a surfactant which is solid at ambient temperatures.

Published European Patent Application 0 256 608 discloses a method for the preparation of a solid, phytoactive composition comprising (a) reacting an acid form of a phytoactive N-phosphonomethyl-N-carboxymethyl compound with a liquid amine to form the amine salt of said N-phosphonomethyl-N-carboxymethyl compound (b) admixing said amine salt of said N-phosphonomethyl-N-carboxymethyl compound with a molten surfactant, the surfactant being solid at ambient temperature and (c) cooling said mixture to a temperature below the melting point of the surfactant to form a composition comprising said surfactant and said amine salt of N-phosphonomethyl-N-carboxylmethyl compound interdispersed in the matrix thereof and which is solid at ambient temperatures.

EPO Publication No. WO 87/04595 discloses a herbicidal water-soluble dry particulate glyphosate formulation comprising the sodium salt of glyphosate and a surface active agent of the formula:

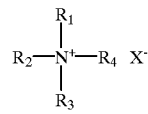

wherein $R_1$ and $R_2$ are independently methyl or ethyl, $R_3$ is methyl, ethyl benzyl or $C_{10}$ to $C_{18}$ alkyl, $R_4$ is $C_{10}$ to $C_{18}$ alkyl and X is chloro or bromo.

Japanese LOP 145 205-88 (the equivalent of EPO274369) discloses an aqueous concentrate herbicidal formulation comprising a water soluble glyphosate salt, ammonium sulfate and a quaternary ammonium salt.

PCT/WO 87-04,712 discloses a method of preparing a particulate alkali metal salt of N-phosphonomethylglycine which comprises adding a solid alkali metal base with agitation to N-phosphonomethylglycine containing up to 25% water.

Research Disclosure Publication 27161 November 1986 "Novel Glyphosate acid wettable powder formulation effective in control of weeds" discloses a formulation comprising N-phosphonomethylglycine, nonionic surfactant, diatomaceous earth, inorganic salt (ammonium sulphate) and an antifoaming agent.

Chemical Abstracts 103: 191395K (1985) Davydov, A. M.; Vechtomova, T. N.; Banzunova, G. G. (USSR). Sashch. Rast. (Moscow) 1985, (9), 40-1 (Russ) discloses that the 36% aq. soln. Utal (I) [96638-41-4] and the 50% wettable powder Fosulen (II) are Soviet brands of glyphosate.

SUMMARY OF THE INVENTION

The invention comprises a dry, water soluble, agriculturally acceptable herbicidal composition comprising a water soluble salt of N-phosphonomethylglycine as a water-dispersible granule, water soluble granule, or water-dispersible powder or water soluble powder although water soluble granules are preferred. The composition comprises a water soluble salt of N-phosphonomethylglycine and additionally one or more liquid surfactants. In another embodiment, the invention further comprises said composition containing water.

Compositions of this invention may further comprise ammonium sulfate, potassium sulfate, potassium chloride, sodium sulfate, urea, mixtures thereof and the like. The composition may optionally include a synergist, quick-burn additive, a humectant, a co-herbicide, a dye, pigment, corrosion inhibitor, thickener, dispersing agent, calcium sequestrant, defoamer, mixtures thereof and the like. When employing two or more herbicides in the composition, the composition of this invention may be a water soluble or a water dispersible granule. If at least one of two or more herbicides employed herein is relatively insoluble in water, likely a water dispersible composition is preferred.

In a process for preparing the composition of this invention, the dry, water soluble, granular, agriculturally acceptable composition is prepared by pan, extrusion, fluid bed (or equivalent) granulation of N-phosphonomethylglycine, and surfactant, or a water soluble salt of N-phosphonomethylglycine, optionally with a surfactant.

In another embodiment of this invention, said composition is prepared by admixing N-phosphonomethylglycine or an agriculturally acceptable salt of N-phosphonomethylglycine with one or more liquid surfactants.

In another method of preparing the compositions of this invention, one may admix ingredients with water and thereafter spray dry to give a granular product.

In another method of preparing the compositions of this invention, one may admix the ingredients with water and drum dry on a flaking roll and grind the flaked composition to give a granular composition.

Yet another method of preparing the granular compositions of this invention involves admixing glyphosate and base, for example ammonium bicarbonate, with water, crystallizing, centrifuging and blending in the surfactant and drying the granular product.

Even yet another method for preparing the granular composition of the invention, involves carrying out the reaction of the ingredients in a fluid bed drier using glyphosate wet cake or moistened glyphosate containing a minimum of moisture to provide occurrence of the neutralization phase of the process and then completion by drying to give the granular product.

Compositions may be optionally mixed with ammonium sulfate and optionally one or more additional herbicides and thereafter these ingredients blended to form said admixed composition. The order of addition of the ingredients to the starting material, typically glyphosate or a water soluble salt thereof is not critical. The admixed composition is optionally granulated with equivalent means or in an equivalent manner to form a composition of this invention.

OBJECTS OF THE INVENTION

It is an object of this invention to provide a dry, water soluble and/or water dispersible, agriculturally acceptable herbicidal composition.

It is an object of this invention to provide a process for preparing said composition.

It is yet another object of this invention to provide a herbicidal method of use for killing and controlling weeds by applying a herbicidally effective amount of said composition to the locus of the plant or weed to be killed or controlled.

It is a further object of this invention to provide a dry, water soluble or water dispersible agriculturally acceptable herbicidal composition which has relatively low shipping costs, mix compatibility with various co-herbicides, mix compatibility with various additives which can be packaged in low cost, combustible containers and is easy to use with minimum user contact with the formulation.

These and other objects such as a uniform particle size distribution and noncaking features are achieved in this invention hereinafter described in more detail.

Another advantage offered in this invention is where a dry product would be of interest in areas of use where worker exposure is an issue. Dry formulations are excellent candidates for packaging in water-soluble bags that would substantially reduce worker exposure from handling and mixing.

DETAILED DESCRIPTION OF THE INVENTION

The invention comprises a dry, water soluble, agriculturally acceptable herbicidal composition comprising a water soluble salt of N-phosphonomethylglycine and (optionally) a liquid surfactant.

As employed herein, the term "liquid" comprises a substance in a flowable state at room temperature (about 25° Centigrade) and includes waxes and liquid compositions containing solid surfactants.

Said composition of this invention is typically greater than about 60 mesh and contains in the range from about 0.1% to about 5.0% weight and preferably less than about 2% weight percent water, although greater or lesser amounts of water (moisture) may be present depending on the composition ingredients.

If desired a co-herbicide, a corrosion inhibitor, a thickener, a dispersing agent, a calcium sequestrant, a synergist, a quick burn down additive, a humectant, a dye or pigment, defoamer may be admixed individually or collectively in the composition.

The thickener may be selected from the group consisting of sodium lignosulfonate, starches, cellulose derivatives, high molecular weight polyoxyethylenes, gums, mixtures thereof and the like.

Certain co-herbicides which form water soluble salts may be used. Such co-herbicides may be selected from the group consisting of acifluorfen (5-(2-chloro-4-(trifluoromethyl)phenoxy-2-nitrobenzoate), chloramben (3-amino-2,5-dichlorobenzoic acid), 2,4-D (2,4-dichlorophenoxy)acetic acid), endothal (7-oxabicyclo(2.2.1)heptane-2,3-dicarboxylic acid), mecoprop ([2-(2-methyl-4-chlorophenoxy) propionic acid], picloram (4-amino-3,5,6-trichloropyridine-2-carboxylic acid), 2,4,5-T(2,4,5-trichloroacetic acid), benzac (2,3,6-trichlorobenzoic acid), dicamba (3,6-dichloroo-anisic acid), MCPA (4-chloro-o-tolyloxyacetic acid), dalapon (2,2-dichloro-propionic acid), dichlorprop (2,4-dichlorophenoxypropionic acid), MCPB (4-(4-chloro-o-tolyloxy)-butyric acid, bialaphos (DL-homoalanin-4-yl-methylphosphinate), glufosinate (Ammonium (3-amino-3-carboxypropyl)-methylphosphinate, Pursuit (2-[4,5-dihydro-4-methyl-4-(1-methylethyl)-5-oxo-1H-imidazel-2-yl]-5-ethyl-3-pyridine carboxylic acid), Scepter (2-[4,5-Dihydro-4-methyl-4-(1-methylethyl)-5-oxo-1H-imidazol-2-yl]-3-quinolinecarboxylic acid), mixtures thereof and the like.

It may be preferred to utilize a solid, water insoluble co-herbicide. In that embodiment, the co-herbicide is present in the composition as a fine powder. Illustrative coherbicides include sulfonylureas such as [Oust (2-[3-(4,6-dimethylpyrimidin-2-yl)ureidosulphonyl]benzoic acid) and Glean (1-(2-chlorophenylsulphonyl)-3-(4-methoxy-6-methyl-1,3,5-triazin-2-yl)urea)], Ally (Methyl 2-[[[[4-methoxy-4-methyl-1,3,5-triazin-2-yl)amino]carbonyl]-amino]-sulfonyl]-benzoate), Classic (Ethyl 2-[(4-chloro-6-methoxy-pyrimidin-2-yl)amino]-carbonyl]amino]-sulfonyl]-benzoate), Diuron (N'-(3,4-dichlorophenyl)-N,N-dimethylurea), Linuron (3-(3,4-dichlorophenyl)-1-methoxy-1-methylurea), atrazine ((2-chloro-4-(ethylamino)-6-(isopropylamino)-s-triazine, simazine (2-chloro-4,6-bis (ethylamino)-5-triazine), mixtures thereof and the like.

The water insoluble co-herbicide may be liquid or solid present in said composition as a water dispersible granule such as atrazine ((2-chloro-4-(ethylamino)-6-(isopropylamino)-s-triazine, fomesafen (5-[2-chloro-4-(trifluoromethyl)-phenoxy]-N-methylsulfonyl)-2-nitrobenzamide), oxyfluorfen (2-chloro-1-(3-ethoxy-4-nitrophenoxy)-4-(trifluoromethyl)benzene), feroe ([fenoxaprop-ethyl: (±)-ethyl-2-[4-(6-cholo-2-benzoxazol-2-yloxy)phenoxy]propanoate simazine, (2-chloro-4,6-bis (ethylamino)-5-triazine), diuron (N'-(3,4-dichlorophenyl)-N,N-dimethylurea), Ally (Methyl 2-[[[[4-methoxy-4-methyl-1,3,5-triazin-2-yl)amino]carbonyl]-amino] sulfonyl]-benzoate), Classic (Ethyl 2-[(4-chloro-6-methoxy-pyrimidin-2-yl)amino]-carbonyl]amino]sulfonyl]-benzoate), Linuron (3-(3,4-dichlorophenyl)-1-methoxy-1-methylurea), Oust (2-[3-(4,6-dimethylpyrimidin-2-yl) ureidosulphonyl]-benzoic acid), Glean (1-(2-chlorophenylsulphonyl)-3-(4-methoxy-6-methyl-1,3,5-triazin-2-yl)urea)], mixtures thereof and the like.

The glyphosate salt component of the compositions of this invention may be preferably prepared by admixing various bases (acid acceptors) including those selected from those listed below with glyphosate wet cake or moistened glyphosate. Ammonia, ammonium hydroxide, ammonium and alkali metal carbonates, bicarbonates, meta borates, citrates, formates, oxalates, phosphates, propionates, pyrophosphates, metasilicates, orthosilicates, sulfites, thiosulfates, tetraborate, monoacid phosphates, tripolyphosphates, metaphosphates, sodium hydroxide, potassium hydroxide, tetrasodium EDTA, mixtures thereof and the like. Mixtures of glyphosate and salts thereof may be employed as starting materials.

As employed herein, the term "admixed" includes reaction, neutralization and partial neutralization of glyphosate as well as mixed with and sprayed on, combined with or added to another ingredient(s).

Suitable liquid surfactants include nonionic surfactants, anionic surfactants, cationic surfactants and amphoteric surfactants, mixtures thereof and the like, preferably ones that provide increased herbicidal activity of N-phosphonomethylglycine. Most preferred surfactant is an ethoxylated tallow amine containing 15–18 moles of ethylene oxide.

Examples of liquid nonionic surfactants are polyoxyethylene alkyether, polyoxyethylene alkylarylether, polyoxyalkylene alkyl arylether formaldehyde condensates, polyoxyethylenealkylene arylether, polyoxyalkylene alkylester, polyoxyalkylene alkyl sorbitan ester, polyoxyalkylene alkyl sorbitol ester, polyoxyalkylene alkyl glycerol ester, polyoxyalkylene block copolymer, polyoxyalkylene blockcopolymer alkyl glycerol ester, polyoxyalkylene alkyl sulfonamides, polyoxyalkylene rosin ester, polyoxypropylene block copolymers, polyoxyethylene oleyl ether, polyoxyalkylene alkylphenols, mixtures thereof and the like.

Examples of liquid cationic surfactants are polyoxyalkylene alkylamines such as ethoxylated tallow amine, ethoxylated oleylamine, ethoxylated soyamine, ethoxylated cocoamine, ethoxylated synthetic alkyl amines, ethoxylated III° octyl amine, etc. and mixtures thereof.

Examples of liquid anionic surfactants (typically solids unless dissolved in water) are sodium alkyl sulfate, sodium mono- and di-alkyl naphthalene sulfonates, sodium alpha-olefin sulfonate, sodium alkane sulfonates, alkylsulfates, polyoxyalkyene alkylether sulfate, polyoxyalkylene alkylarylether sulfates, polyoxy-alkylene styrylphenylether sulfate, mono- and di-alkylbenzene sulfonates, alkylnaphthalene sulfonate, alkylnaphthalene sulfonate formaldehyde condensate, alkyl diphenylether sulfonates, olefine sulfonates, alkylphosphates, polyoxyalkylene alkyl phosphates, polyoxyalkylene phenylether phosphate, polyoxyalkylphenol phosphates, poly-carboxylates, fatty acids salts, stearic acid and salts thereof, oleic acid and salts thereof, N-methyl fatty acid taurides, mixtures thereof and the like, including sodium, potassium, ammonium and amine salts.

Examples of suitable amphoteric surfactants are lauryldimethylamine oxide, Aromox C/12, amine oxides, Monaterics, Miranols, betaines, Lonzaines, other amine oxides, mixtures thereof and the like.

Preferable agriculturally acceptable salts of N-phosphonomethylglycine (glyphosate) include the ammonium, isopropylamine, trimethylsulfonium, imminourea salts, sodium, potassium, mixtures thereof and the like. The sodium and ammonium salts of N-phosphonomethylglycine are especially preferred in this invention. Mixtures of water soluble salts of N-phosphonomethylglycine may be employed herein as well as surfactant salts of N-phosphonomethylglycine including, for example, a N,N,bishydroxyethylcocoamine salt of N-phosphonomethylglycine, Most preferred water-soluble granules (WSGs) are those made with the ammonium salt or sodium salt of glyphosate and an ethoxylated tallowamine surfactant (tallowamine+ 15–20 moles of ethylene oxide) as the surfactant.

In another embodiment the composition of this invention further comprises ammonium sulfate, potassium sulfate, potassium chloride, sodium sulfate, urea, mixtures thereof and the like.

If desired, a dry, water soluble, agriculturally acceptable composition comprising a water soluble, agriculturally acceptable salt of N-phosphonomethylglycine may be prepared by pan granulation or extrusion granulation of the salt of glyphosate itself. If pan granulation is to be employed, an intermediate drying step after preparing the salt may be necessary before pan granulation is carried out.

The salt of N-phosphonomethylglycine may be prepared by admixing an acid acceptor with glyphosate acid (containing in the range from about 10 to about 15 wt % water) to neutralize the N-phosphonomethylglycine. A slight excess of acid acceptor may be preferred, however it is not required when ammonia, ammonium, hydroxide or ammonium bicarbonate is the base.

When the composition of this invention comprises a water soluble salt of glyphosate, the process of preparation comprises preparing said water soluble salt of glyphosate followed by granulation (pan, extrusion, fluidized bed, or equivalent such as spray drying, drum drying, flaking, crystallizing and centrifuging) to form a composition of this invention. In this embodiment, water is added in a pan granulation step to promote granulation and is thereafter removed in subsequent drying. If extrusion granulation is employed then a water removal step is usually but not always necessary.

A fluidized bed drying step is usually carried out following granulation to form a composition of this invention. Reworking of the granules may be necessary at times to take into account various parameters such as temperature, ingredient quality, and the like.

When the composition of this invention includes a liquid surfactant the process of preparation comprises admixing said water soluble, agriculturally acceptable salt of N-phosphonomethylglycine and said one or more liquid surfactants optionally with ammonium sulfate and thereafter blending these ingredients singularly or collectively to form an admixed composition as a composition of this invention.

The surfactant (s) may be admixed with the water soluble salt of glyphosate by spraying the surfactant on the water soluble salt of glyphosate while the water soluble salt of glyphosate is being pan granulated to form a composition of this invention. The one or more liquid surfactants may be admixed with the water soluble glyphosate salt as in a blender prior to granulation. In the latter embodiment, water is typically added to the granulator to promote granulation in forming a composition of this invention.

If desired in another embodiment, water may be sprayed onto the admixed composition comprising water soluble salt of glyphosate and optionally surfactant while said admixed composition is being pan granulated to form a composition of this invention.

Typically the admixed composition will have an appearance (depending on the amount of water present at that time) which ranges from a damp or moist powder, even fluffy, to that of a dough like substance after the admixing is completed in a kneader, blender or other mixer type device. Thereafter additional water present in the mixed composition may be removed to a satisfactory level for granulation (pan, extrusion, fluid bed or equivalent) which may in turn be followed by fluidized bed drying. Carbon dioxide and water are removed in the drying process.

If extrusion granulation is desired, an admixed composition may be fed to an extruder without an intermediate drying and-thereafter the extrusion product, the extruded admixed composition, may be further dried in a fluidized bed dryer or other drying equipment (drying oven, flash dryer, etc.) to form a composition of this invention.

This invention also includes a method of killing or controlling weeds by applying a herbicidally effective amount of the composition of this invention to the locus of the plant or weed to be killed or controlled. Dilution with water before application to the locus of the plant or weed is desirable although perhaps not necessary in all cases as for example when the plants contain a dew. In general when killing or controlling weeds or plants using this invention, the general methods of use disclosed in U.S. Pat. No. 3,799,458 for salts and compositions employing glyphosate and the other patents referred to hereinabove will be useful to those of skill in the art.

The application of an effective amount of the compounds of this invention to the plant is essential for the practice of the present invention. The exact amount of glyphosate salt containing glyphosate as the active ingredient to be employed is dependent upon the response desired in the plant as well as such other factors as the plant species and stage of development thereof, and the amount of rainfall as well as the specific salt employed. In foliar treatment for the control of vegetative growth, the active ingredients are applied in amounts from about 0.01 to about 20 or more pounds per acre. In applications for the control of aquatic plants, the active ingredients are applied in amounts of from about 0.01 part per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, and patents referred herein the approximate application rate. Granules may also be applied using conventional broadcast granule techniques.

The following examples are presented to illustrate the present invention as well as some of the various embodiments of the invention. These examples are presented as being illustrative of the novel formulations, process for preparing the invention and and herbicidal use thereof and are not intended to be a limitation of the scope of this invention.

EXAMPLES

General Admixing Process:

In a typical process for preparing ammonium glyphosate water soluble granules (and optionally sodium glyphosate) water soluble granules of this invention, the process begins by neutralizing glyphosate acid wet cake (contains about 1 to about 15% water) with ammonium bicarbonate (or sodium carbonate or sodium bicarbonate) an admixing process in a mixer such as a ribbon blender or a Hobart type mixer to form a water soluble salt of glyphosate (ammonium or sodium salt of glyphosate).

The products of the reaction include ammonium (sodium) glyphosate, carbon dioxide and water. As the reaction proceeds there is a loss in weight of the formulation. If desired, the reaction can be monitored by the rate of carbon dioxide formation and consequential weight loss. The time involved for the reaction to proceed to completion is from about twenty to thirty minutes to about one hour. The optimum particle size is about 20 mesh for the admixed composition.

After the glyphosate ammonium (sodium) bicarbonate reaction has been completed, a fluffy wet cake or white powder of ammonium (sodium) glyphosate has formed. At the time, the ammonium (sodium) glyphosate can either be subsequently formulated into a water soluble granule to form a composition of this invention or dried, or used as is for some other use such as in package mixes to also form a composition of this invention.

(Optional) Surfactant Addition and Mixing

After making the ammonium (sodium) glyphosate as described above, one optionally adds at least one surfactant. The preferred surfactant is an ethoxylated fatty tallow amine with an average ethylene oxide content of about 15–18 moles (MON-0818). The addition of surfactant typically produces a very stiff dough. The mixing equipment is appropriately selected so as not only be capable of mixing a thick, stiff dough, but it must also be steam jacketed to allow heating to drive off excess water to form a damp powder in the event pan granulation is to follow as a further processing step. Depending on the amount of water present, the admixed composition at this step can be a composition of this invention.

Pan Granulation

If desired, the moist but free flowing ammonium (sodium) glyphosate surfactant mixture is fed into a typical pan granulator and granulated to form a composition of this invention. Water is usually added in the granulation step. In order to achieve the desired granule characteristics it may be desirable to experiment with the granulator's operating characteristics.

Another approach is to granulate the ammonium glyphosate in a piece of equipment known as a turbulator which is basically a modified pug mixer that mixes thoroughly. The powder is added at one end. Liquid is sprayed on during mixing which forms granules that come out the other end and are ready for drying. This approach could be used in place of the surfactant addition and mixing step to combine the mixing step with the granulating step. Other suitable methods of granulating could be fluid bed granulation, tumble granulation techniques, or granulating using Schugi granulation equipment.

II. Methods of Granulation

A number of different methods were used to make WSGs. Some WSGs were made by spraying a liquid surfactant directly on ammonium glyphosate powder in a pan granulator (or disk pelletizer). It was found that the surfactants could be mixed with the glyphosate powder in a blender and this mixture granulated by spraying water onto the powder. There was little difference in the granule quality. Other equipment used in the making of granules included: Patterson-Kelley V-blenders, Extruders, Ribbon Blenders, and Fluid Beds.

Extrusion Granulation

If desired, one may proceed from the first step to extrusion granulation. In that embodiment, the admixed product from the admixing device is fed to an extruder and the extruded product of this invention is typically a cylindrical shaped particle, typically having a diameter in the range from about 0.4 to about 2.0 mm and preferably in the range from about 0.7 to 1.2 mm and having a length in the range from about 1 to 10 mm and preferably from about 2 mm. to about 5 mm.

After granulation, further drying of the composition is typically desired to form a composition of this invention.

Drying

A preferable method of drying is the use of a fluid bed drier which allows drying to occur quickly and more temperate than other methods. For small size samples, drying can be accomplished in a 60° C. to 70° C. in a few hours or in an oven overnight.

The water content of the sodium glyphosate powder was also found to have an effect on the size granules formed in a pan granulator and on the quality of the WSG. Sodium glyphosate powder can be a free flowing powder while containing as much as about 18–20% water. It was found that a minimum water content of about 5–7% was needed to form granules of good quality. About 10 to 15% were found to be the optimum water content. When the water content was below about 5–7% for pan granulation the sodium and ammonium glyphosate granules that would form would be extremely soft and powdery on the inside.

Water could be employed in the glyphosate powder to be granulated or, if desired, the surfactant can be mixed with water that is sprayed on the powder. Even when the water was contained in the surfactant, an optimum water content for granulation was one in which the total amount of water amounted to approximately 10% of the glyphosate weight.

A minimum water content was found to be necessary even when the process to make the granules was changed such that the surfactant was blended in a mixer with the ammmonium glyphosate powder and the resultant powder granulated. When "bone dry" ammonium glyphosate was mixed with Sterox NJ (nonyl phenol+9.5 moles EO) and the resulting powder granulated, the granules were soft. If the ammonium glyphosate contained about 10% water when the surfactant was mixed in, the granules formed were of very good quality.

The water seems to be necessary only while the granules are forming. Once the granules are formed, the water can be removed by drying and the granules will be high quality, sturdy granules.

The water can be removed either in an oven or fluid bed drier.

Without being bound by theory, the relationship between water, surfactant ethylene-oxide (EO) content and granule quality seems to suggest a hydrogen bonding or hydration between the surfactant and glyphosate. Surfactants that do not gel in water, in general, do not yield granules of good quality.

The following examples were prepared in general accordance with the above general procedures although departures were employed to adjust for batch size and general equipment availability. The identity and quantity of ingredients are provided for each composition. All percents (%) are on a weight basis.

Example 1

Ammonium bicarbonate was admixed with glyphosate acid and the mixture was thereafter dried to form a composition of this invention.

| | |
|---|---|
| Glyphosate acid (100%) | 90.86 grams |
| Ammonium bicarbonate | 43.52 |
| Water and carbon dioxide lost | −35.38 grams |
| | 100.00 grams |

Example 2

| | |
|---|---|
| Glyphosate Acid wet cake (86%) | 105.65 grams |
| Ammonium bicarbonate | 43.52 grams |
| | 149.17 grams |

The above ingredients were weighed together and mixed in a beaker with a spatula to form ammonium glyphosate. The temperature of mixture dropped. The final temperature was 7° C. Weight steadily decreased.

Final loss while mixing after about 2 hours on a Roller Mill was 21.76 grams.

The ammonium glyphosate was dried in an 60° C. oven overnight.

Loss 22.41 grams.

Total weight 105.00 grams

Example 3

To the ammonium glyphosate (prepared in Example 2 above) was added 30 grams of MON-0818 and hand mixed. The resultant mixture was a solid. MON-0818 surfactant was absorbed onto the granules. The resulting formulation was

| | |
|---|---|
| Ammonium Glyphosate (95%) | 105 grams |
| MON-0818 | 30 grams |
| | 135 grams |

Example 4

A similar composition was prepared as above, except Genamine T-150 (tallow amine plus 15 moles ethylene oxide (E.O.) was used. Again, a dry solid was formed.

| | |
|---|---|
| Ammonium glyphosate | 65% wt. |
| Genamine T-150 | 23% |
| Ammonium Xylene Sulfonate | 20 |
| Water and inerts | 10 |

The formulation was prepared by first adding Genamine T-150 to wet cake glyphosate and mixing by hand. Ammonium bicarbonate was added. Reaction seemed much slower and incomplete.

The combining of T-150 (tallow amine+15 mole E.O.) with water in the glyphosate wet cake appeared to make water less available for dissolving ammonium bicarbonate and reacting with the wet cake.

Ammonium xylene sulfonate 40 (AXS-40) was added and mixed into the formulation to thin out the gel structure. Weight loss increased at a similar rate as without T-150. The amount of AXS-40 in the final formulation was 7%. The mixture was dried in 60° oven.

Example 5

Ammonium glyphosate was made by adding ammonium bicarbonate to wet cake (see Example 2).

This time the formulation was dried before adding Genamine T-150. Again, theoretical weight loss agreed well with actual weight loss.

Genamine T-150 was added at 25% level of the formulation and mixed in. The formulation was not dry and free flowing. The sample was placed in 60° C. oven overnight. The sample was still gooey.

Another sample was prepared. Again, similar results were obtained. 25% water (in regard to formulation) was sprayed on and mixed in. The formulation heated up, not significantly, but noticeably. The sample was placed in 60° C. oven overnight. Dry chunks of free flowing solid were formed.

Example 6

| Formulation | |
|---|---|
| Ammonium Glyphosate | 64.64% |
| Ethomeen T-25* | 25.30% |
| TH Antifoam 30 Ind** | 1.02% |
| Water & Inerts | 8.86% |
| | 100.00% |

*Tallowamine + 15EO
**Silicone defoamer

This composition was prepared by hand with a beaker and a spatula.

Assayed at 60.64% glyphosate.

Example 7

| Formulation | |
|---|---|
| Ammonium Glyphosate | 56.95% |
| Ethomeen T-25 | 28.05% |
| Sodium Lauryl Sulfate | 5.00% |
| TH Antifoam 30 Ind | 1.02% |
| Water & Inerts | 8.08% |
| | 100.00% |

This composition was prepared by a beaker and a spatula.

Example 8

Several samples of glyphosate granules were made with different levels of surfactant and ammonium sulfate. Pan granulation was employed.

Procedure:
1. Make ammonium glyphosate wet cake in Hobart mixer or mix in pan granulator.
2. Add surfactant to ammonium glyphosate wet cake, while mixing in pan granulator.
3. Add ammonium sulfate while mixing.
4. Screen to 8/40 mesh.

| | |
|---|---|
| Glyphosate Acid wet cake (85%) | 107.06 grams |
| Ammonium Bicarbonate | 40.91 grams |
| | 147.97 grams |
| Weight loss $CO_2$ | −22.50 grams |
| | 125.47 grams |

II. For making 2000 grams of acid equivalent formulation:

| | |
|---|---|
| Glyphosate wet cake Acid 85% | 2352.94 grams |
| Ammonium Bicarbonate | 899.10 grams |
| | 3252.04 grams |
| $CO_2$ loss | 494.50 grams |
| | 2757.54 grams |

Example 9

| | |
|---|---|
| Glyphosate wet cake acid (85%) | 19.3% |
| Ammonium bicarbonate | 7.4% |
| Ammonium sulfate | 74.25% |
| MON-0818 surfactant | 6.88% |

Water and carbon dioxide came off

Attempted to pan granulate, but the presence of ammonium sulfate is detrimental to granulation properties. Product granulated by adding ammonium lignin sulfonate at 2% level.

Example 10

| | |
|---|---|
| Mon 0818 | 6.67 grams |
| Ammonium glyphosate | 20.0 grams |
| Ammonium sulfate | 60.0 grams |
| Reax 836A* | 2.0 grams |

*Lignosulfonate dispersant

Example 11

| | % |
|---|---|
| Ammonium salt of glyphosate (90%) | 13.3 |
| Linuron 90% | 22.2 |
| Ammonium sulfate | 20.0 |
| Sodium sulfate | 36.5 |
| White carbon | 1.5 |
| Runox 1000C* | 5.0 |
| Sorpol 5175* | 1.5 |

*Proprietary anionic sulfates

Example 12

| | |
|---|---|
| Ammonium glyphosate (91% acid equivalent) | 800 grams |
| Water | 50 grams |
| Ethomeen C-15 | 150 grams |

Initial pan and extrusion granulation looked good.

Example 13

| | |
|---|---|
| Ammonium glyphosate | 250 grams |
| Sorbitol (solid) humectant | 250 grams |
| Ethomeen T-25 liquid surfactant | 80 grams |

Example 14

This formulation was made by adding solids in a jar and then mixing on roller mill.

| | |
|---|---|
| Glyphosate acid wet (86%) | 250 grams |
| Ammonium bicarbonate | 90 grams |
| Ammonium sulfate (granular) | 600 grams |
| Mixed these for 1 hour. | |
| Sprayed on Ethomeen T-25 | 67 grams |
| Dried after T-25 was added. | |

The above composition was made in a Patterson Kelley Blender.

Example 15

Ammonium glyphosate was prepared from glyphosate using the ammonia bicarbonate method in a ribbon mixer. Three hundred pounds of glyphosate wet cake acid was dryed by placing it in 2 inch high trays and leaving it open to the air. The dry glyphosate acid was then Fitz milled to uniform size. Initial moisture was about 16%, after 2 days in the open the moisture content was 1.25%.

| | |
|---|---|
| Glyphosate acid | 150 pounds |
| Ammonium bicarbonate | 70 pounds |
| Water | 4 pounds |
| Flo Mo TA-15* | 17 pounds |

*Tallowamine + 15 E.O.

The ammonium bicarbonate was added as by hand as lumps to glyphosate acid in the ribbon mixer. Water was added to speed up the reaction. The reaction took 2.5 hours. Some ammonia bicarbonate lumps were left which needed to be broken up for better reaction rates. The final mixture was Fitz-milled to breakup the lumps. Additional granulation was not needed.

Example 16

Using the same ribbon mixer as in Example 15, a step up was attempted. For the first trial dry glyphosate acid was used.

| | |
|---|---|
| Ammonium sulfate | 150 pounds |
| Glyphosate acid (97%) | 51.5 pounds |
| Ammonium bicarbonate | 12.0 pounds |
| Water | 4.0 pounds |

These four ingredients were mixed together and then FLOMO TA-15 (17.0 pounds) was added to make a total of 234.5 pounds. This produced good mixing and allowed lumps to be broken up. Good granules formed upon drying.

Example 17

Using ammonium glyphosate wet cake "V blender" granulation was carried out. The blender gave a dusty granule. Pan granulation was very fast. Particles were 87% less than 4 mesh.

Example 18

| | |
|---|---|
| Ammonium sulfate | 11125 grams |
| Glyphosate acid | 2500 grams |
| Ammonium bicarbonate | 560 grams |

| | |
|---|---|
| Ethomeen T-25 | 1042 grams |
| Water and carbon dioxide loss | −663 grams |

The formulation was made in Patterson Kelley blender with the water content at 2.94%. Granulates were fine in size.

Example 19

| | |
|---|---|
| Ammonium glyphosate (86.5%) | 83.24% |
| Ethomeen T-25 | 16.76% |

Made 7000 grams in Patterson Kelley blender

Example 20

| | |
|---|---|
| Ammonium glyphosate (86.5%) | 23.13% |
| Ethomeen C-12* | 6.67% |
| Ammonium sulfate | 70.20% |

*Cocoamine + 2 E.O.

Example 21

| | |
|---|---|
| Glyphosate wet cake acid (85%) acid equivalent | 23.53% |
| Ammonium sulfate | 72.3% |
| Ammonium bicarbonate | 4.5% |
| Ethomeen C-12 | 6.7% |
| Carbon dioxide and water loss | −7.03% |

Made in Patterson Kelley blender

Example 22

Made a water soluble and water dispersible combination with glyphosate and Scepter herbicides.

Steps:
1. Using ammonium glyphosate wet cake from the ammonium bicarbonate reaction (Example 8) as the glyphosate source, Scepter was milled (hammermilled through 0.1211 screen,) and the two were mixed together in the roller mill mixer. Ethomeen T-25 was slowly added and mixed in. Granules formed. Granules were soft so 10% water was added sprayed on while granules were mixing on roller mill. Mixing continued for 1.5 hours spatula was used to clean mixture off the walls of the jar while mixing. Granules were dried overnight at 60° in an oven. Granules were screened to 12/20 mesh. Large granules were crushed and again screened through 12/20 mesh screens. Fines were reworked into another batch to demonstrate reworking. In one embodiment sieves can be employed or if desired, a Sweco screening system can be used. Oversize can be ground using a Hammermill or a grinding unit with ceramic balls for example.

| | |
|---|---|
| Ammonium glyphosate (80% wet cake) | 71.85 grams |
| Scepter (88%) | 16.63 grams |
| Ethomeen T-25 | 18.90 grams |
| Water | 10.7 grams |

Placed in an oven overnight at 60° C., weight was 102.3 grams.

Example 23

| | |
|---|---|
| Glyphosate acid wet cake (87%) | 1150 grams |
| Ammonium bicarbonate | 450 grams |
| Classic technical (98.75%) | 50 grams |
| Ethomeen T-25 | 333 grams |

Carbon dioxide given off as solids were mixed and reacted was 247.5 grams

Water taken off during drying was 161.25 grams Procedure employed:

All dry materials were added and mixed. Mixture became cold (7° C.) and lost weight. Reaction took about 1.5 hours.

Dried, reacted materials (ammonium glyphosate and 20 Classic) were put in pan granulator and granulated while Ethomeen T-25 was sprayed on.

Granulated glyphosate/Classic was then dried in vibrating fluid bed. Granules are screened to 8/40 mesh size.

Granules dissolved/dispersed in 1–2.5 minutes at 2 RPS (revolution per second) 5 grams of granules were dispersed in 95 grams tap water and agitated with a stirring rod by hand.

Example 24

| | |
|---|---|
| Diuron technical 99% | 46.13% |
| Ammonium glyphosate/surfactant * (65% acid equivalent) | 23.43% |
| Ammonium sulfate | 30.44% |

* Milled blend of 78% ammonium glyphosate and 22% Ethomeen T-25 (65% acid equivalent)

Example 25

| | |
|---|---|
| Diuron (99%) | 39.63% |
| Ammonium glyphosate/surfactant * | 60.37% |

* Milled blend of 78% ammonium glyphosate and 22% Ethomeen T-25 (65% acid equivalent)

Example 26

| | |
|---|---|
| Diuron 99% | 22.25% |
| Ammonium glyphosate/surfactant * | 33.90% |
| Ammonium sulfate | 43.85% |

* Milled blend of 78% ammonium glyphosate and 22% Ethomeen T-25 (65% acid equivalent)

Example 27

| | |
|---|---|
| Atrazine (Shell Airmilled) (94%) | 60.60% |
| Stepanol Me-dry sodium * | 1.50% |
| Morwet D-425 ** | 3.29% |
| Ammonium glyphosate/surfactant *** | 34.61% |
| | 100.00% |

* sodium lauryl sulfate
** sodium sulfonate of a naphthalene formaldehyde condensate
*** Milled blend of 78% ammonium glyphosate and 22% Ethomeen T-25 (65% acid equivalent)

The above ingredients were admixed in the order listed until uniform in a plastic bag. The admixed composition was granulated using pan granulator. Water was sprayed during granulating and a standard pan granulation procedure was used. The granules were dried in a lab fluidized bed.

Example 28

| | % |
|---|---|
| Ammonium Glyphosate (86.5% a.e.) | 89.30 |
| Oxyfluorfen technical (95%) | 10.70 |
| | 100.00 |

Composition converted into extruded granules.

Example 29

| | % |
|---|---|
| Glyphosate wet cake (86%) | 22.0 |
| Diammonium phosphate | 14.0 |
| Sorpol 7553 | 6.0 |
| Ammonium sulfate | 58.0 |
| | 100.00 |

Example 30

| | % |
|---|---|
| Ammonium Glyphosate (90% a.e.) | 20.0 |
| Dicamba sodium salt (90% a.e.) | 10.0 |
| Texapon K-1296* | 9.0 |
| Ammonium sulfate | 60.4 |
| Cellogen 4H** | 0.6 |
| | 100.00 |

*Sodium lauryl sulfate (Henkel)
**Carboxymethyl cellulose

Example 31

| | % |
|---|---|
| Glyphosate wet cake (91.0%) | 22.4 |
| Sodium bicarbonate | 9.5 |
| Sorpol 7553 | 6.0 |
| Ammonium sulfate | 73.0 |
| | 100.00 |

Example 32

| | % |
|---|---|
| Glyphosate wet cake (85%) | 22.4 |
| Sodium hydroxide | 4.5 |
| Sorpol 7553 | 6.0 |
| Ammonium sulfate | 73.0 |
| Water lost or drying | −5.9 |
| | 100.00 |

Example 33

| | % |
|---|---|
| Glyphosate wet cake (82.2%) | 20.42 |
| Dicamba (88.8%) | 9.34 |
| Sodium bicarbonate | 18.95 |
| Sorpol 7553* | 4.15 |
| Monoammonium phosphate | 47.14 |
| | 100.00 |

*Tallowamine + 15EO

Example 34

| | % |
|---|---|
| Glyphosate wet cake (81.2%) | 28.38 |
| Sodium bicarbonate | 11.48 |
| Ammonium sulfate | 5.18 |
| Sorpol 7553 | 54.96 |
| | 100.00 |

Example 35

| | % |
|---|---|
| Glyphosate (96%) | 30.35 |
| Ammonia | 2.62 |
| Witconate AOK * | 8.09 |
| Ammonium sulfate | 58.28 |
| SAG-47 ** | 0.66 |
| | 100.00 |

* Sodium tetradecyl and hexadecyl-sulfate
** Silicone defoamer

Example 36

|  | % |
|---|---|
| Ammonium glyphosate * | 72.09 |
| Sterox NJ ** | 27.01 |
|  | 100.00 |

\* Prepared from glyphosate wet cake and ammonium bicarbonate
\*\* Nonyl phenol + 9.5 EO

Example 37

|  | % |
|---|---|
| Glyphosate wet cake (85%) | 23.05 |
| 2,4-D (99%) | 20.02 |
| Texapon K1296 * | 5.00 |
| Ammonium sulfate | 50.02 |
| Sodium bicarbonate | 17.05 |
| Water and CO$_2$ lost | −16.05 |
|  | 100.00 |

\* sodium lauryl sulfate

Example 38

|  | % |
|---|---|
| Sodium glyphosate | 16.07 |
| Sorpol 7553 | 3.04 |
| Ammonium sulfate | 46.06 |
| Bialaphos WSG (20% a.e.) * | 37.03 |
|  | 100.00 |

\* Herbiace WSG

Example 39

|  | % |
|---|---|
| Ammonium glyphosate | 73 |
| Surfactant * | 22 |
| Water | 5 |
|  | 100 |

\* 3:1 blend of Sterox NK (nonyl phenol + 11 E.O.):Aromox C-12 (N,N-bis(hydroxyethyl)cocoamine oxide)

Example 40

|  | % |
|---|---|
| Ammonium glyphosate | 1000 lbs. |
| T-DET N-307 * | 500 lbs. |
| Water loss on drying | −173 lbs. |

\* Nonylphenol + 30 moles E.O.

A spray dry process for preparation of the granular product of this invention involves use of a feed stock consisting of an aqueous solution or slurry or combination thereof of the ingredients (glyphosate salt, or glyphosate and base, surfactant and-additives such as ammonium sulfate, a solid co-herbicide such as atrazine, etc., if desired) with a total solids content of 45–65%.

The spray tower size may vary greatly from a pilot unit of 6' diameter×15' height to a commercial unit of 22' diameter× 30' vertical height or larger equipped with a 30°–60° collection cone, if desired.

Temperature of slurry: 20–50° C.
Spray mode: Mixed flow or co-current Laminar.
Atomization Nozzle: Hollow cone (1–3 nozzles)
Spray Pressures: 60–250 psi
Air Flow: 625–4200 CFM
Tower Air Temperature:
  Inlet: 250–400° F.
  Outlet: 100–300° F.

Examples prepared via a spray dry process are Nos. 41–45. Examples 20–25 also may be prepared via a spray dry process.

Example 41

|  | % |
|---|---|
| Sodium glyphosate | 25.09 |
| Ammonium sulfate | 68.04 |
| Witconate AOK | 5.07 |
|  | 100.00 |

Example 42

|  | % |
|---|---|
| Ammonium glyphosate | 27.40 |
| Ammonium sulfate | 72.60 |
|  | 100.00 |

Example 43

|  | % |
|---|---|
| Ammonium glyphosate | 25.04 |
| Ammonium sulfate | 68.09 |
| Witconate AOK | 5.07 |
|  | 100.00 |

Example 44

|  | % |
|---|---|
| Ammonium glyphosate | 27.04 |
| Ammonium sulfate | 72.06 |
|  | 100.00 |

Example 45

|  | % |
|---|---|
| Sodium glyphosate | 27.05 |
| Ammonium sulfate | 72.05 |
|  | 100.00 |

Ingredients may be admixed in the order listed until uniform in a plastic bag. The admixed composition may be granulated using pan granulator. Water can be sprayed on during granulating and a standard pan granulation procedure used. The granules may be dried in a lab fluidized bed.

Although this invention has been described with respect to specific embodiments, the details thereof are not to be construed as limitations, for it will be apparent that various equivalents, changes and modifications may be resorted to without departing from the spirit and scope of this invention. It is understood that such equivalent embodiments are intended to be included within the scope of this invention.

What is claimed is:

1. A dry water-soluble agriculturally acceptable herbicidal composition in granular form comprising N-phosphonomethylglycine or a water soluble salt of N-phosphonomethylglycine, at least one surfactant which in its neat form is liquid at 25° C. and which gels in water and which enhances the bioefficacy, and less than about 5% by weight water.

2. The composition of claim 1 wherein said water soluble salt of N-phosphonomethylglycine is the sodium, potassium or ammonium salt or a mixture thereof.

3. The composition of claim 2 wherein said water present in said composition is in the range from about 0.2 to about 2.0 percent by weight of the total composition.

4. The composition of claim 3 wherein said liquid surfactant comprises a nonionic surfactant, an anionic surfactant, a cationic surfactant, an amphoteric surfactant or mixtures thereof.

5. The composition of claim 4 wherein said nonionic surfactant is a polyoxyethylene polyoxypropylene block copolymer, an alkylphenol polyoxyethylene ether, polyoxyethylene oleylether, or mixtures thereof.

6. The composition of claim 4 wherein said cationic surfactant is an ethoxylated fatty amine surfactant, or surfactant mixtures based thereon.

7. The composition of claim 4 wherein said amphoteric surfactant is an amine oxide, Aromox C/12, betaine, Lonzaine, or mixtures thereof.

8. The composition according to claim 7, further comprising ammonium sulfate, potassium sulfate, potassium chloride, sodium sulfate, urea, or mixtures thereof.

9. The composition of claim 8 which further comprises at least one additional formulating ingredient selected from the group consisting of a dispersing agent, a corrosion inhibitor, a thickener, a calcium sequestrant, a defoamer, a synergist, a quick burn additive, a humectant, a dye or pigment, or combinations thereof.

\* \* \* \* \*